United States Patent
Cheng et al.

(10) Patent No.: US 8,999,522 B2
(45) Date of Patent: Apr. 7, 2015

(54) 6H-INDOLO[2,3-B]QUINOXALINE DERIVATIVES AND ORGANIC LIGHT EMITTING DIODE USING THE SAME

(75) Inventors: Chien-Hong Cheng, Hsinchu (TW); Chun-Hsiang Fan, Hsinchu (TW)

(73) Assignee: National Tsing Hua University, Hsinchu (TW)

(*) Notice: Subject to any disclaimer, the term of this patent is extended or adjusted under 35 U.S.C. 154(b) by 359 days.

(21) Appl. No.: 12/891,460

(22) Filed: Sep. 27, 2010

(65) Prior Publication Data

US 2011/0303901 A1 Dec. 15, 2011

(30) Foreign Application Priority Data

Jun. 15, 2010 (TW) .............................. 99119429 A

(51) Int. Cl.
*H01L 51/54* (2006.01)
*C07F 9/6561* (2006.01)
(Continued)

(52) U.S. Cl.
CPC ............ *C07F 9/6561* (2013.01); *C07D 487/04* (2013.01); *C07F 7/0812* (2013.01); *H01L 51/0059* (2013.01); *H01L 51/0072* (2013.01); *H01L 51/0085* (2013.01); *H01L 51/0094* (2013.01); *H01L 51/5012* (2013.01); *H01L 51/5048* (2013.01); *H01L 51/5096* (2013.01)

(58) Field of Classification Search
None
See application file for complete search history.

(56) References Cited

U.S. PATENT DOCUMENTS

2003/0057827 A1* 3/2003 Kido et al. .................... 313/504

FOREIGN PATENT DOCUMENTS

JP 02108058 A * 4/1990 ............... G03G 5/06

OTHER PUBLICATIONS

Watanabe et al. (Tetrahedron Lett. 41 (2000) 481).*
Przyjazna et al. Polymer 2004, 45, p. 2559.*
English abstracts for JP 02108058 A.*
(Continued)

*Primary Examiner* — J. L. Yang
(74) *Attorney, Agent, or Firm* — Muncy, Geissler, Olds & Lowe, P.C.

(57) ABSTRACT

A 6H-indolo[2,3-b]quinoxaline derivative has a structure of formula (I). $R^9$ is a member selected from the group consisted of an aryl group having one or more substituents and a heteroaryl group having one or more substituents, and $R^1$ to $R^8$ are substituents. The 6H-indolo[2,3-b]quinoxaline derivative of the present invention incorporates an indole and a quinoxaline group therefore inherits good energy transfer ability from indole and good electron-injection ability from quinoxaline. The compound of the present invention may function as a host material or a dopant in the light-emitting layer. In addition, the compound of the present invention may function as hole transport material, electron transport material, hole blocking material, electron blocking material, hole injecting material or electron injecting material.

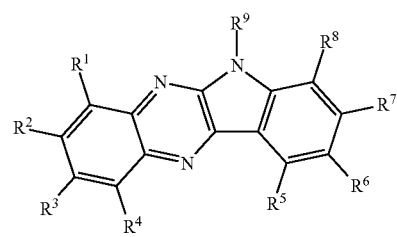

(I)

20 Claims, 1 Drawing Sheet

(51) Int. Cl.
*C07D 487/04* (2006.01)
*C07F 7/08* (2006.01)
*H01L 51/00* (2006.01)
*H01L 51/50* (2006.01)

(56) References Cited

OTHER PUBLICATIONS

English abstracts for JP 02108058 A (1990).*

* cited by examiner

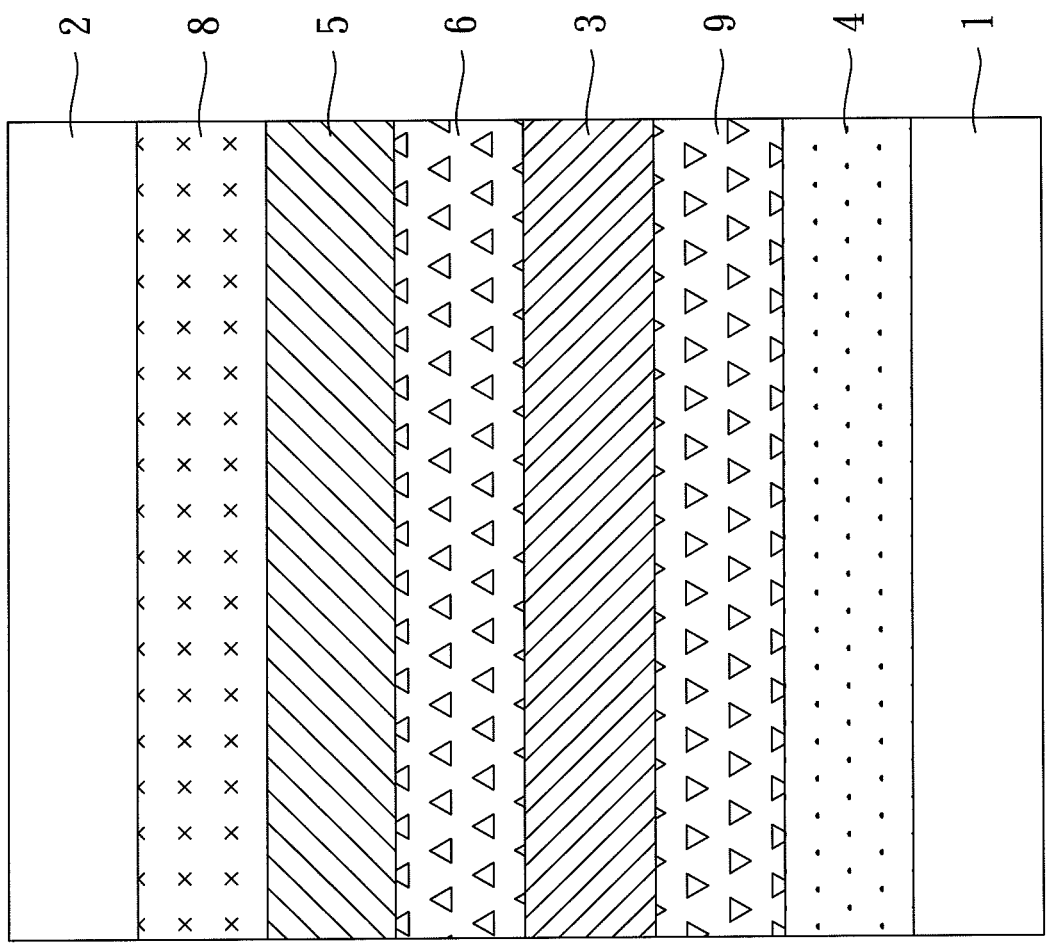

6H-INDOLO[2,3-B]QUINOXALINE DERIVATIVES AND ORGANIC LIGHT EMITTING DIODE USING THE SAME

BACKGROUND OF THE INVENTION

1. Field of the Invention

The present invention relates to a novel compound and organic light emitting diode using the same, particularly to 6H-indolo[2,3-b]quinoxaline derivative and organic light emitting diode using the same.

2. Description of the Prior Art

OLED works on the principal that electrons and holes diffuse through an electron transport layer (ETL) and hole transport layer (HTL), respectively, to enter an light-emitting layer, and recombine in the emitting region to form a particle generally referred as exciton. In order for the exciton to relax to the ground state, the energy is given off in the form of photo radiation. The radiation color can be tuned by applying different emitting materials. OLED has been highly-regarded due to a lot of advantages, such as self illumination, wider visual angle (>170°), shorter response time (~μs), higher contrast, higher efficiency, lower power consumption, higher brightness, lower operative voltage (3-10V), thinner size (<2 mm), flexibility and so on.

The exciton generated from recombining holes and electrons may have triplet state or singlet state for its spin state. The singlet exciton relaxation would radiate fluorescence, and the triplet exciton relaxation would radiate phosphorescence. The phosphorescence has triple lighting efficiency in comparison to fluorescence, and metal complexes may be used in the emitting layer so as to form strong spin-orbital coupling, whereby combined singlet and triplet excited states causes elevated IQE (internal quantum efficiency), 100%, within the device. Therefore, phosphorescent metal complexes have been used as phosphorescent dopants in light-emitting layer. In addition, by using a doping method in the emitting layer, self-quenching of the emitting materials can be reduced greatly to enhance the efficiency of the device. Therefore, the search for proper phosphorescent host materials becomes noteworthy since host materials must be capable of capturing carriers and have good energy transfer properties, high glass transition temperature, high thermal stability and appropriate energy gap of the singlet and triplet excited states. However, it would be difficult to search for host materials that fully meet the criteria and there is still some room for host materials development in OLED.

To sum up, to develop novel host materials is now a current goal.

SUMMARY OF THE INVENTION

The present invention is directed to 6H-indolo[2,3-b)]quinoxaline derivative and organic light emitting diode using the same.

According to one embodiment, a 6H-indolo[2,3-b]quinoxaline derivative includes a chemical formula represented by Formula (I):

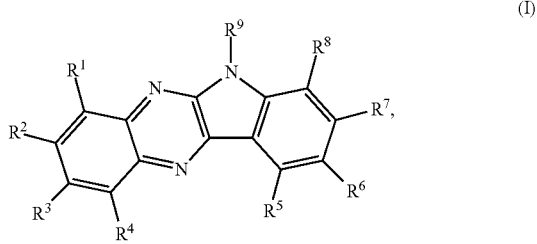

wherein $R^9$ is selected from the group consisted of an aryl group having one or more substituents and a heteroaryl group having one or more substituents; each of $R^1$ to $R^8$ and substituents of $R^9$ is independently selected from the group consisted of hydrogen, halogen, aryl group, alkenyl group, C1-C20 alkyl group, alkynyl group, cyano, trifluoromethyl, alkylamino, amino, alkoxy group, heteroaryl group, halogen substituted aryl group, halogen substituted aralkyl group, haloalkyl substituted aryl group, haloalkyl substituted aralkyl group, aryl substituted C1-C20 alkyl group, cycloalkyl group C1-C20 alkoxy group, C1-C20 alkyl substituted amino group, haloalkyl substituted amino group, aryl substituted amino group, heteroaryl substituted amino group, aryl substituted phosphine oxide, C1-C20 alkyl substituted phosphine oxide, haloalkyl substituted phosphine oxide, halogen substituted phosphine oxide, heteroaryl substituted phosphine oxide, nitro group, carbonyl group, aryl substituted carbonyl group, heteroaryl substituted carbonyl group, and halogen substituted C1-C20 alkyl group.

According to another embodiment, an organic light emitting diode includes a cathode, an anode and an organic layer configured between the cathode and the anode and comprising the aforementioned 6H-indolo[2,3-b]quinoxaline derivative.

According to still another embodiment, a synthetic method of a 6H-indolo[2,3-b]quinoxaline derivative is performed according to the following reaction formula.

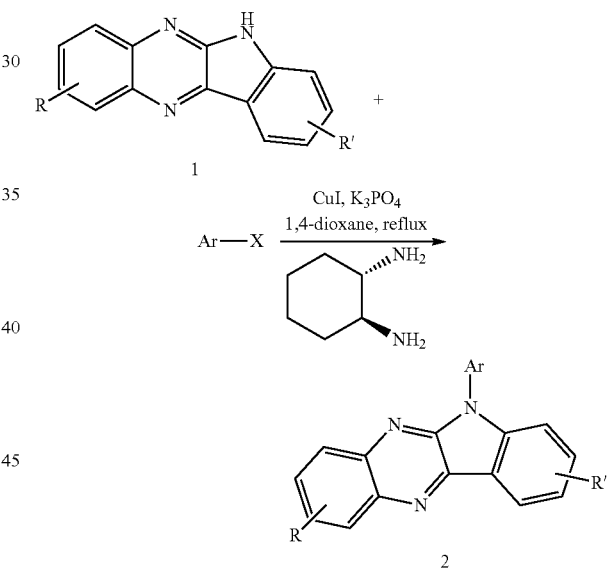

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein:

FIG. 1 is a schematic diagram illustrating an organic light emitting device containing 6H-indolo[2,3-b]quinoxaline derivatives according to one embodiment of the present invention.

DESCRIPTION OF THE PREFERRED EMBODIMENT

The present invention is directed to 6H-indolo[2,3-b]quinoxaline derivative and organic light emitting diode using the same.

Referring to Formula (I), 6H-indolo[2,3-b]quinoxaline derivatives of the present invention are illustrated.

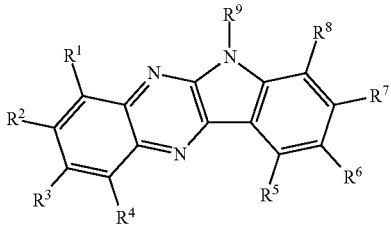

(I)

$R^9$ is selected from the group consisted of an aryl group having one or more substituents and a heteroaryl group having one or more substituents. The aryl group, for example, may be phenyl, naphthyl, diphenyl, anthryl, pyrenyl, phenanthryl, fluorene or other polyphenyl. The heteroaryl group, for example, may be pyrane, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline or other heteroaryl groups.

Each of $R^1$ to $R^8$ and substituents of $R^9$ is independently selected from the group consisted of hydrogen, halogen, aryl group, alkenyl group, C1-C20 alkyl group, alkynyl group, cyano, trifluoromethyl, alkylamino, amino, alkoxy group, heteroaryl group, halogen substituted aryl group, halogen substituted aralkyl group, haloalkyl substituted aryl group, haloalkyl substituted aralkyl group, aryl substituted C1-C20 alkyl group, cycloalkyl group C1-C20 alkoxy group, C1-C20 alkyl substituted amino group, haloalkyl substituted amino group, aryl substituted amino group, heteroaryl substituted amino group, aryl substituted phosphine oxide, C1-C20 alkyl substituted phosphine oxide, haloalkyl substituted phosphine oxide, halogen substituted phosphine oxide, heteroaryl substituted phosphine oxide, nitro group, carbonyl group, aryl substituted carbonyl group, heteroaryl substituted carbonyl group, and halogen substituted C1-C20 alkyl group.

In one preferred embodiment, $R^9$ is a phenyl group, and 6-phenyl-6H-indolo[2,3-b]quinoxaline derivatives of the present invention are provided and represented by formula (II):

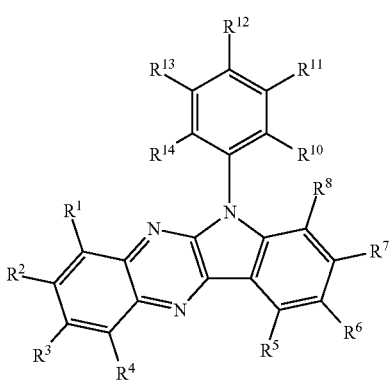

(II)

Each of $R^{10}$ to $R^{14}$ is independently selected from the group consisted of hydrogen, halogen, aryl group, alkenyl group, C1-C20 alkyl group, alkynyl group, cyano, trifluoromethyl, alkylamino, amino, alkoxy group, heteroaryl group, halogen substituted aryl group, halogen substituted aralkyl group, haloalkyl substituted aryl group, haloalkyl substituted aralkyl group, aryl substituted C1-C20 alkyl group, cycloalkyl group, C1-C20 alkoxy group, C1-C20 alkyl substituted amino group, haloalkyl substituted amino group, aryl substituted amino group, heteroaryl substituted amino group, aryl substituted phosphine oxide, C1-C20 alkyl substituted phosphine oxide, haloalkyl substituted phosphine oxide, halogen substituted phosphine oxide, heteroaryl substituted phosphine oxide, nitro group, carbonyl group, aryl substituted carbonyl group, heteroaryl substituted carbonyl group, and halogen substituted C1-C20 alkyl group.

It has been reported that quinoxaline derivatives have good electron mobility, and ultra low lowest unoccupied molecular orbital (LUMO); thus the electron could be injected easily. Therefore, Quinoxaline derivatives are suitable and efficient candidates for electron transporting layer.

The compounds of the present invention contain 6H-indolo[2,3-b]quinoxalin moiety, which incorporates indole and quinoxaline moiety and contains high thermal stability and good energy transfer ability from indole moiety and good electron-injection ability from quinoxaline moiety. Application of 6H-indolo[2,3-b]quinoxalin derivatives of the present invention may include a host emitting material, a guest emitting material, an electron transport material, or a hole transport material in an organic electronic device.

For better thermal stability, energy transfer, electron transport and/or hole transport capability, the $R^9$ substituent of Formula (I) and $R^{10}$ to $R^{14}$ of Formula (II) may be one of following chemical formulas listed below,

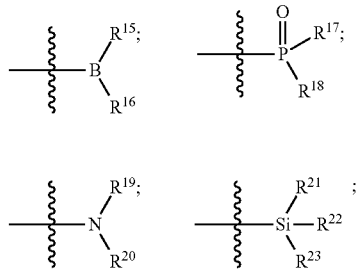

for example, triphenylsilane, diphenylphosphine oxide and diphenylamine.

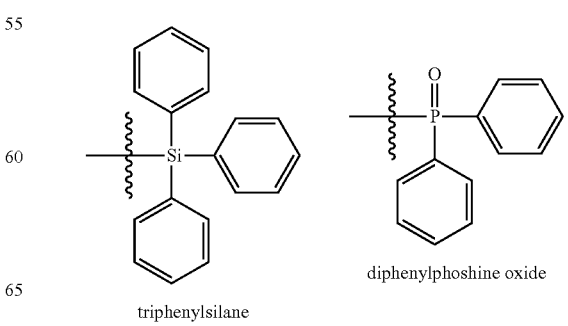

triphenylsilane diphenylphoshine oxide

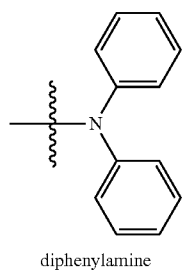

diphenylamine

Alternatively, $R^{10}$ to $R^{14}$ of Formula (II) may have formulas listed below.

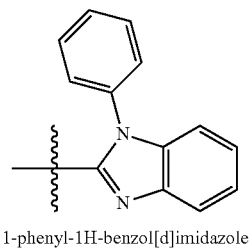   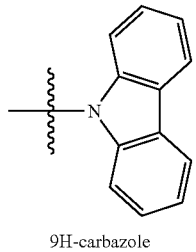

1-phenyl-1H-benzol[d]imidazole     9H-carbazole

In one embodiment, a dimer of 6H-indolo[2,3-b]quinoxaline may be provided; for example, one of $R^{10}$ to $R^{14}$ is selected from the group consisted of 6H-indolo[2,3-b]quinoxaline, 6-phenyl-6H-indolo[2,3-]quinoxaline, 6-(biphenyl-4-yl)-6H-indolo[2,3-b]quinoxaline.

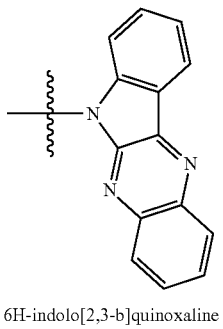

6H-indolo[2,3-b]quinoxaline

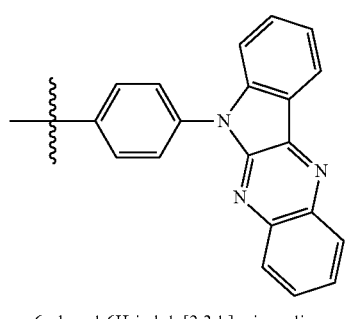

6-phenyl-6H-indolo[2,3-b]quinoxaline

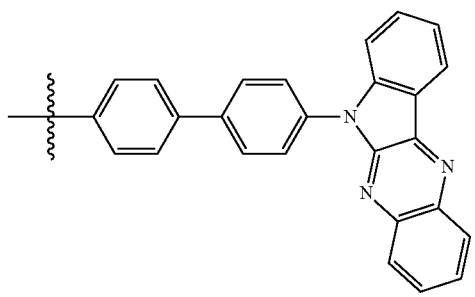

6-(biphenyl-4-yl)-6H-indolo[2,3-b]quinoxaline

In one embodiment, 6H-indolo[2,3-b]quinoxaline derivative compound may include bis(4-(6H-indolo[2,3-b]quinoxalin-6-yl)phenyl)diphenylsilane or 6,6'-(4,4'-(9H-fluorene-9,9-diyl)bis(4,1-phenylene))bis(6H-indolo[2,3-b]quinoxaline).

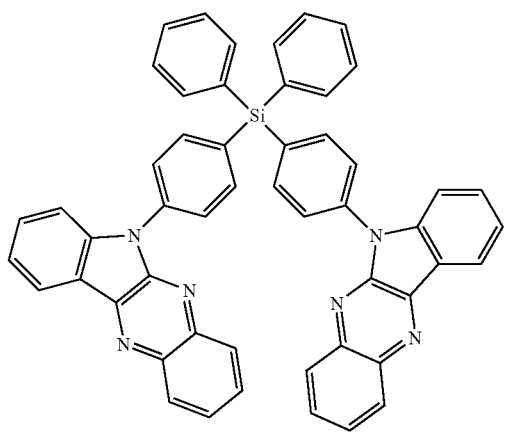

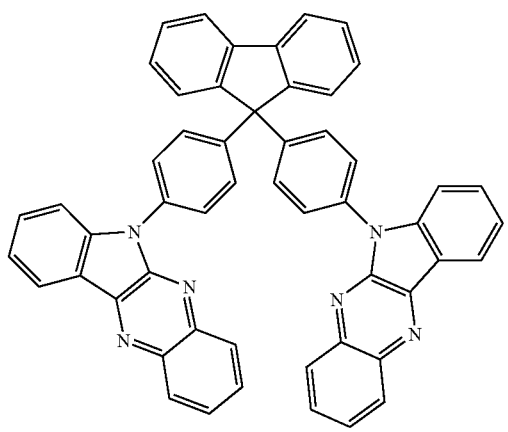

The synthetic method of 6H-indolo[2,3-b]quinoxaline derivatives of the present invention is now provided.

Compound Synthesis

Referring to a reaction formula listed below, 6H-indolo[2,3-b]quinoxaline derivate 1 is synthesized with reactants o-phenylenediamine and isatin derivates in the acidic solution at a yield of 99%, where the H⁺ provider of the acidic solution may be acetic acid, hydrogen chloride, sulfuric acid or nitric acid.

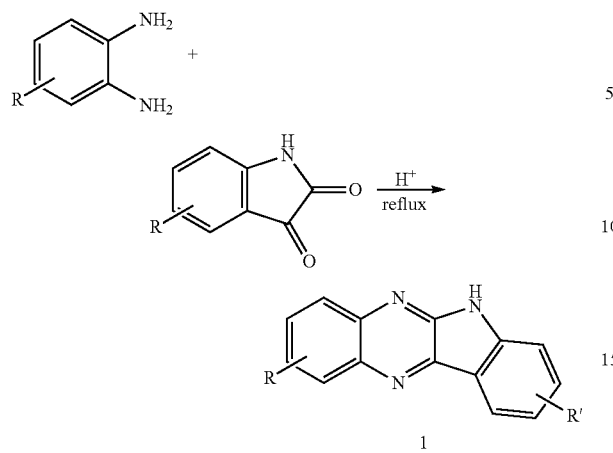

R and R' may be chosen from the combinations of substituents $R^1$ to $R^8$.

The 6H-indolo[2,3-b]quinoxaline derivative 2 having aromatic moiety is obtained by reaction of compound 1 and the aromatic compound with various R" and X substituents in a basic solution and the reaction formula is listed below.

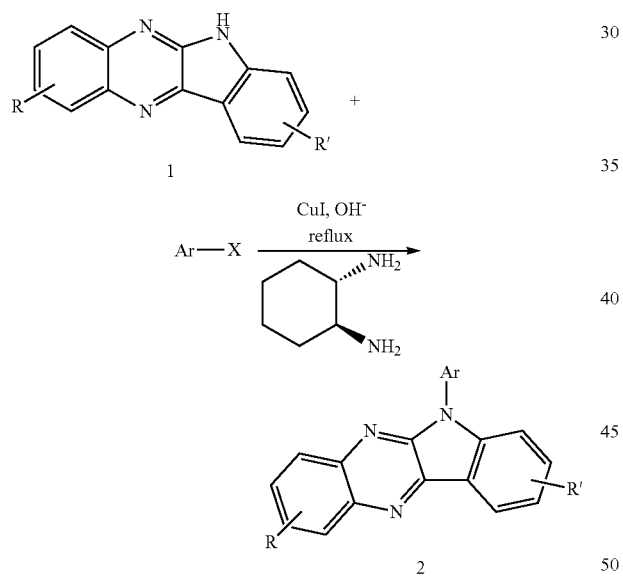

The solvent of the basic solution comprises 1,4-dioxane, DMSO (dimethyl sulfoxide), toluene, THF (tetrahydrofuran), N,N-dimethylformamide or acetonitrile. The OH⁻ provider of the basic solution comprises potassium phosphate, sodium phosphate, potassium carbonate, sodium carbonate, cesium carbonate, sodium tert-butoxide, potassium hydroxide or sodium hydroxide. The reaction is catalyzed by copper iodide having a (±)-trans-1,2-diaminocyclohexane ligand to obtain the compounds of the present invention.

In one embodiment, preferably, the aromatic compound Ar is a phenyl compound, and 6-phenyl-6H-indolo[2,3-b]quinoxaline derivative 3 is obtained from reaction of compound 1 and a phenyl compound with various substituents R" and X in a basic solution.

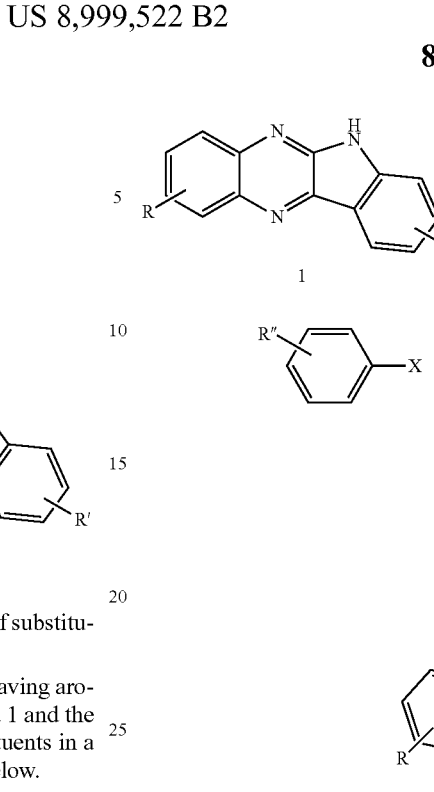

wherein the R" is selected from the above mentioned combinations of $R^{10}$ to $R^{14}$.

X is selected from the group consisted of halogen, hydrogen, alcoholes, tosylates, diazonium salts, nonaflates, triflates, fluorosulfonates, mesylates, nitrate, phosphate, tetraalkylammonium salts, ethers, esters, acid anhydrides, ammonium, phenoxides and carboxyl acids Examples of 6H-indolo[2,3-b]quinoxaline derivates of the present invention are now further specified and described. However, the scope of the present invention is not thus limited with these examples and should refer to the appended claims.

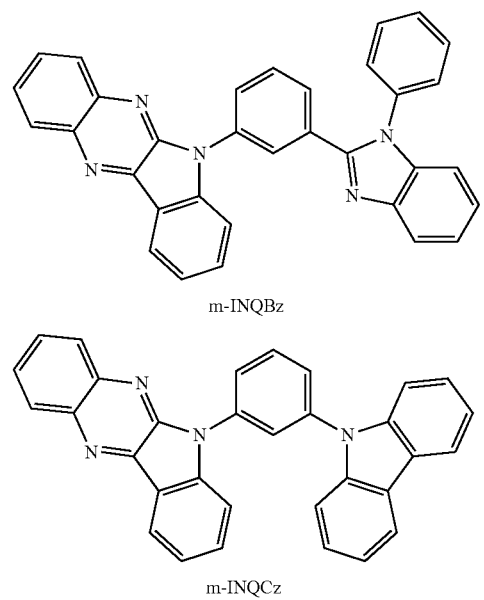

m-INQBz m-INQCz

-continued
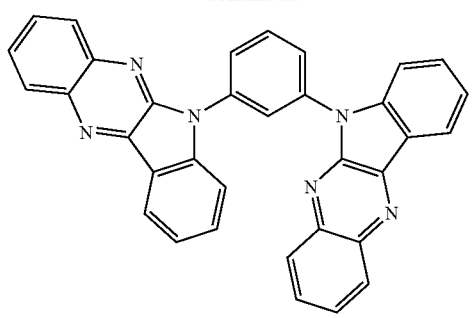
mDINQ
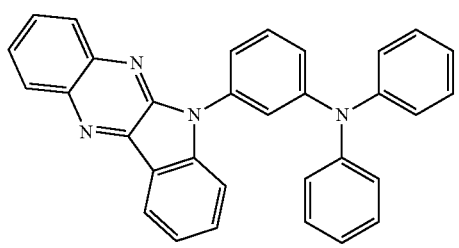
m-INQDA
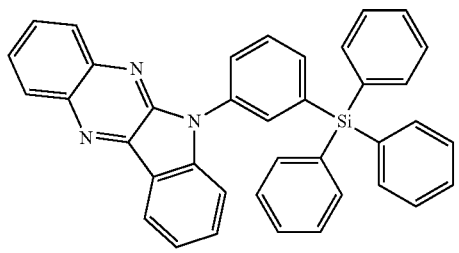
m-INQSi
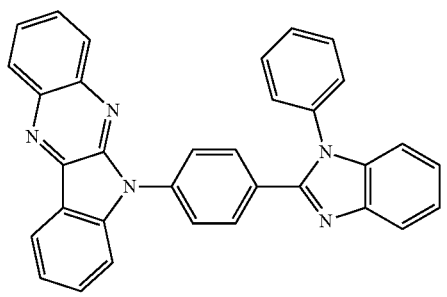
p-INQBz
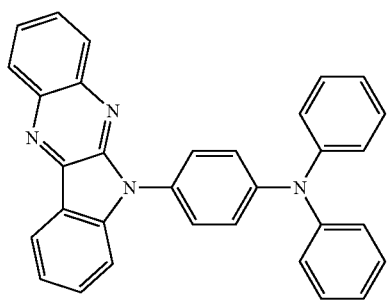
p-INQDA
-continued
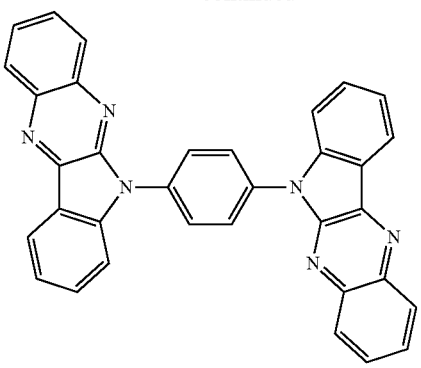
pDINQ
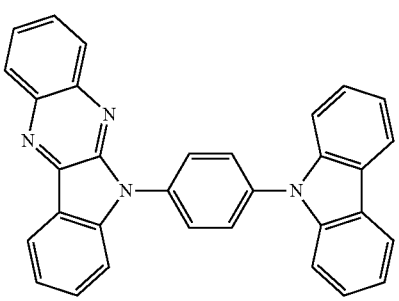
p-INQCz
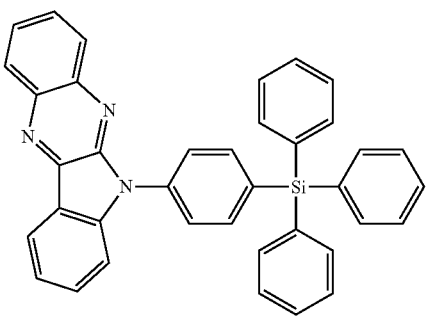
p-INQSi
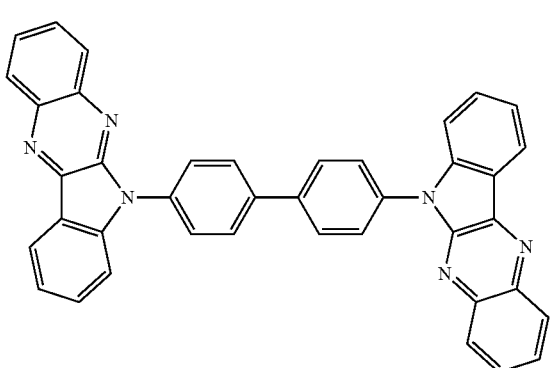
DPINQ -continued

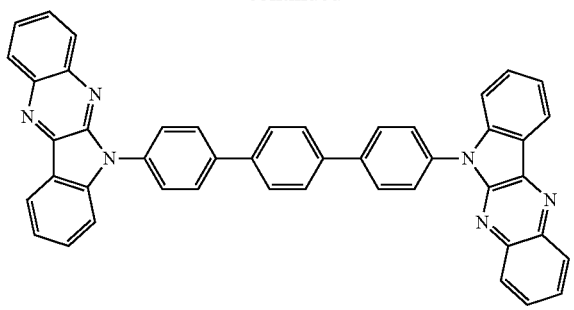

TPINQ

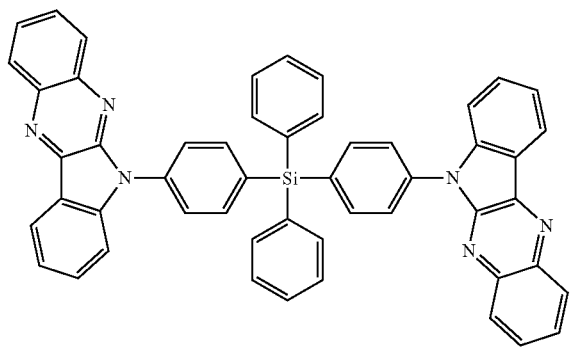

2INQ

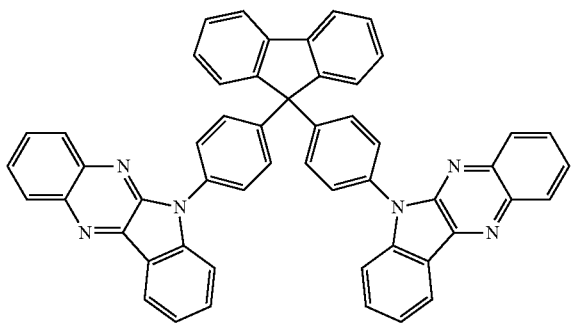

FINQ

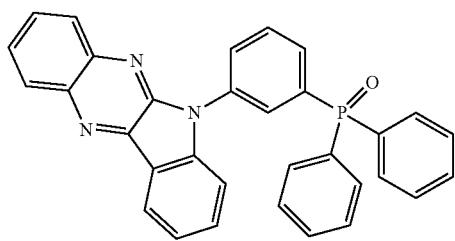

m-INQPO

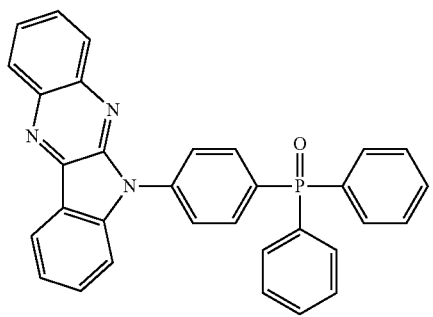

p-INQPO

-continued

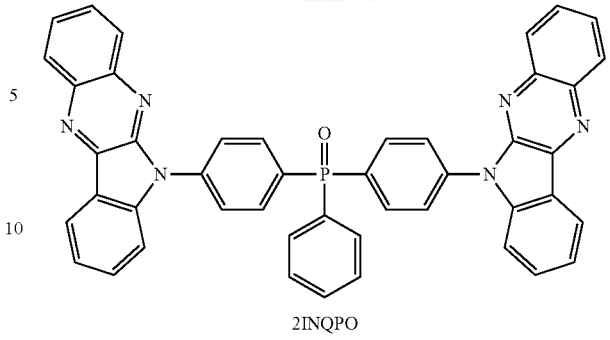

2INQPO

EXAMPLE 1

6-(3-(1-phenyl-1H-benzo[d]imidazol-2-yl)phenyl)-6H-indolo[2,3-b]quinoxaline (hereinafter abbreviated as m-INQBz, yield rate: 87%)

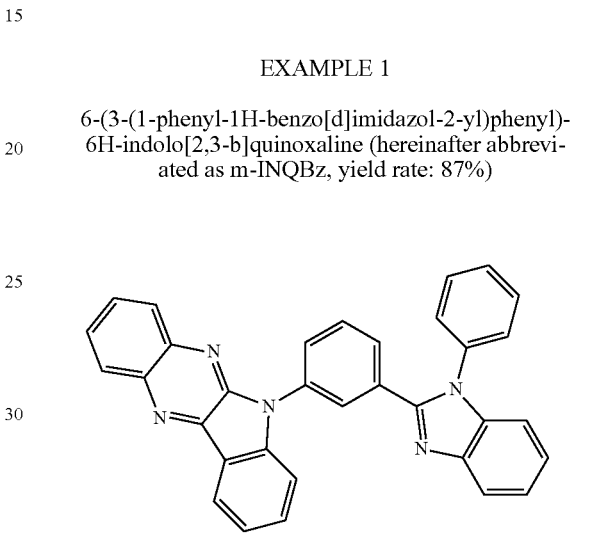

$^1$H NMR (400 MHz, CDCl$_3$, δ[ppm]):8.49(d, J=8.0 Hz, 1H), 8.30(m, 1H), 8.06(m, 1H), 7.87(m, 2H), 7.79(m, 2H), 7.71(m, 2H), 7.63(t, J=8.0 Hz, 1H), 7.54(m, 4H), 7.42(m, 3H), 7.33(m, 1H), 7.26(m, 2H), 7.07(d, J=8.0 Hz, 1H) $^{13}$C NMR (100 MHz, CDCl$_3$, δ[ppm]): ☐151.25, 145.56, 144.185, 142.87, 140.33, 139.97, 139.76, 137.35, 136.81, 135.45, 131.67, 130.99, 130.14, 129.88, 129.15, 128.79, 128.70, 128.29, 127.56, 127.52, 126.55, 123.17, 122.54, 121.87, 119.95, 119.76, 110.50, 110.33. HRMS (FAB, m/z): [M$^+$] calcd. for C$_{33}$H$_{21}$N$_5$, 487.1797. found 487.1795.

EXAMPLE 2

6-(3-(9H-carbazol-9-yl)phenyl)-6H-indolo[2,3-b]quinoxaline (hereinafter abbreviated as m-INQCz, yield rate: 95%)

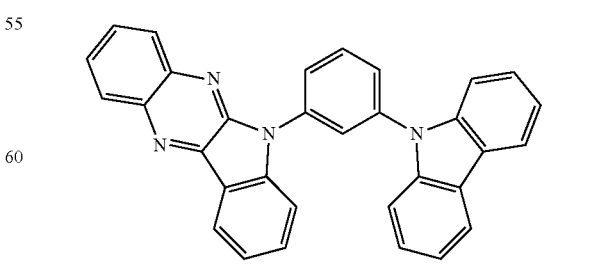

$^1$H NMR (400 MHz, CDCl$_3$, δ[ppm]): 8.58 (d, J=7.6 Hz, 1H), 8.35(m, 1H), 8.18(m, 1H), 8.15 (d, J=7.6 Hz, 2H), 8.11

(m, 1H), 7.85(m, 5H), 7.75(m, 3H), 7.69(m, 1H), 7.49(m, 3H), 7.32(t, J=7.6 Hz, 2H) $^{13}$C NMR (100 MHz, CDCl$_3$, δ[ppm]): 145.44, 143.83, 140.38, 139.97, 139.88, 138.95, 136.77, 131.03, 130.64, 129.24, 128.97, 128.05, 126.67, 126.03, 125.22, 125.19, 124.32, 123.62, 122.77, 122.12, 120.30, 120.04, 110.52, 109.99. HRMS (FAB, m/z): [M$^+$] calcd. for C$_{32}$H$_{20}$N$_4$, 460.1688. found 460.1692.

EXAMPLE 3

1,3-di(6H-indolo[2,3-b]quinoxalin-6-yl)benzene (hereinafter abbreviated as mDINQ, yield rate: 97%)

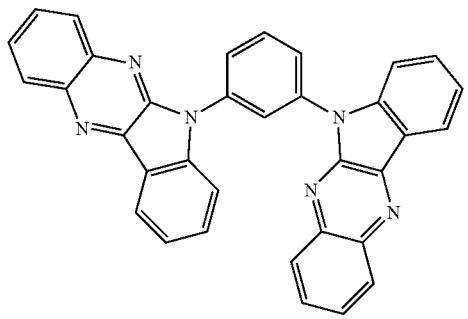 [SMILES: c1cc(-n2c3ccccc3c3nc4ccccc4nc32)cc(-n2c3ccccc3c3nc4ccccc4nc32)c1]

$^1$H NMR (400 MHz, CDCl$_3$, δ[ppm]):8.61(d, J=8.0 Hz, 2H), 8.37(d, J=8.0 Hz, 2H), 8.19(s, 1H), 8.18(d, J=8.0 Hz, 2H), 8.03(d, J=8.4 Hz, 2H), 7.96(m, 3H), 7.78(m, 6H), 7.50(t, J=7.6 Hz, 2H). HRMS (FAB, m/z): [M$^+$] calcd. for C$_{34}$H$_{20}$N$_6$, 512.1749. found 512.1747.

EXAMPLE 4

3-(6H-indolo[2,3-b]quinoxalin-6-yl)-N,N-diphenyl-benzenamine (hereinafter abbreviated as m-INQDA, yield rate: 97%)

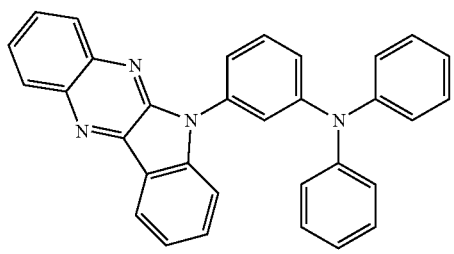 [SMILES: c1ccc(N(c2ccccc2)c2cccc(-n3c4ccccc4c4nc5ccccc5nc43)c2)cc1]

$^1$H NMR (400 MHz, CDCl$_3$, δ[ppm]):8.44(d, J=8.0 Hz, 1H), 8.27(m, 1H), 8.07(m, 1H), 7.78(m, 1H), 7.72(m, 1H), 7.64(t, J=7.2 Hz, 1H), 7.51(m, 2H), 7.42(t, J=7.2 Hz, 1H), 7.34(m, 6H), 7.26(m, 4H), 7.17(m, 1H), 7.07(t, J=7.6 Hz, 2H). $^{13}$C NMR (100 MHz, CDCl$_3$, δ[ppm]): 149.12, 147.32, 145.65, 144.43, 140.55, 140.03, 139.66, 136.13, 130.39, 130.17, 129.41, 129.17, 128.79, 128.20, 126.48, 124.91, 123.51, 122.66, 121.81, 121.11, 120.05, 119.77, 110.69. HRMS (FAB, m/z): [M+H]$^+$ calcd. for C$_{32}$H$_{23}$N$_4$, 463.1923. found 463.1932.

EXAMPLE 5

6-(4-(triphenylsilyl)phenyl)-6H-indolo[2,3-b]quinoxaline (hereinafter abbreviated as p-INQSi, yield rate: 79%)

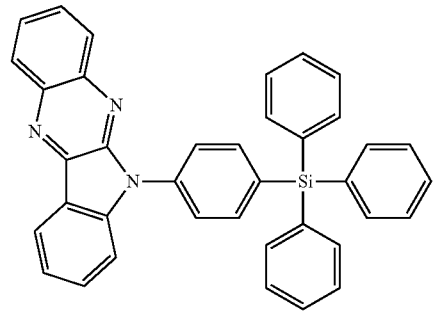 [SMILES: c1ccc([Si](c2ccccc2)(c2ccccc2)c2ccc(-n3c4ccccc4c4nc5ccccc5nc43)cc2)cc1]

$^1$H NMR (400 MHz, CDCl$_3$, δ[ppm]): 8.58(d, J=8.0 Hz, 1H), 8.35(d, J=8.0 Hz, 1H), 8.09(m, 1H), 7.85(d, J=8.0 Hz, 2H), 7.85(d, J=8.0 Hz, 2H), 7.74(m, 2H), 7.66(m, 8H), 7.47 (m, 10H). $^{13}$C NMR (100 MHz, CDCl$_3$, δ[ppm]): 145.66, 144.39, 140.49, 140.18, 139.78, 137.70, 136.66, 134.17, 133.83, 131.02, 129.80, 128.87, 128.21, 128.01, 126.59, 126.02, 122.72, 122.00, 119.97, 110.80. HRMS (FAB, m/z): [M$^+$] calcd. for C$_{38}$H$_{27}$N$_3$Si, 553.1974. found 553.1968.

EXAMPLE 6

6-(4-(9H-carbazol-9-yl)phenyl)-6H-indolo[2,3-b]quinoxaline (hereinafter abbreviated as p-INQCz, yield rate: 88%)

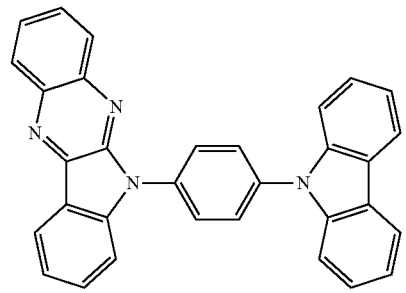 [SMILES: c1ccc2nc3c(nc2c1)c1ccccc1n3-c1ccc(-n2c3ccccc3c3ccccc32)cc1]

$^1$H NMR (400 MHz, CDCl$_3$, δ[ppm]): 8.58(d, J=8 Hz, 1H), 8.34(m, 1H), 8.17(m, 3H), 8.01(m, 2H), 7.88(m, 2H), 7.77(m, 2H), 7.70(m, 2H), 7.61(d, J=8.0 Hz, 2H), 7.50(m, 3H), 7.33(t, J=7.6 Hz, 2H). HRMS (FAB, m/z): [M+H]$^+$ calcd. for C$_{32}$H$_{21}$N$_4$, 461.1766. found 461.1775.

EXAMPLE 7

4-(6H-indolo[2,3-b]quinoxalin-6-yl)-N,N-diphenyl-benzenamine (hereinafter abbreviated as p-INQDA, yield rate: 95%)

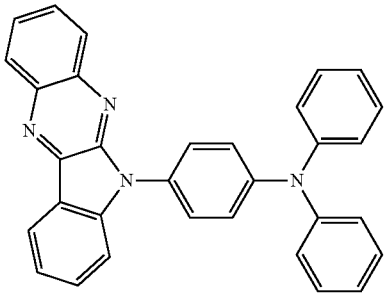 [SMILES: c1ccc(N(c2ccccc2)c2ccc(-n3c4ccccc4c4nc5ccccc5nc43)cc2)cc1]

$^1$H NMR (400 MHz, CDCl$_3$, δ[ppm]): 8.48(d, J=7.2 Hz, 1H), 8.29(m, 1H), 8.07(m, 1H), 7.71(m, 3H), 7.56(m, 3H), 7.44(m, 1H), 7.36(m, 4H), 7.30(m, 2H), 7.24(m, 4H), 7.11(m, 2H). HRMS (FAB, m/z): [M+H]$^+$ calcd. for C$_{32}$H$_{23}$N$_4$, 463.1923. found 463.1915.

EXAMPLE 8 bis(4-(6H-indolo[2,3-b]quinoxalin-6-yl)phenyl) diphenylsilane (hereinafter abbreviated as 2INQ, yield rate: 73%)

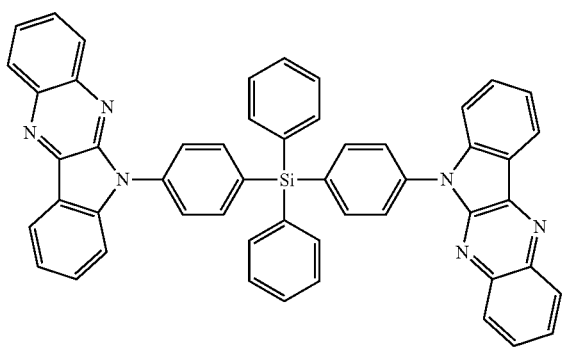 [SMILES: c1ccc([Si](c2ccccc2)(c2ccc(-n3c4ccccc4c4nc5ccccc5nc43)cc2)c2ccc(-n3c4ccccc4c4nc5ccccc5nc43)cc2)cc1]

$^1$H NMR (400 MHz, CDCl$_3$, δ[ppm]):8.55 (d, J J=8.0 Hz, 2H), 8.32 (m, 2H), 8.10 (m, 2H), 7.95 (d, J=8.0 Hz, 4H), 7.85 (d, J=8.0 Hz, 4H), 7.77-7.65 (m, 12H), 7.51-7.45 (m, 8H). $^{13}$C NMR (100 MHz, CDCl$_3$, δ[ppm]): 145.67, 144.36, 140.50, 140.22, 139.84, 137.79, 136.90, 136.54, 133.73, 133.48, 131.05, 130.04, 129.25, 128.91, 128.18, 126.64, 126.15, 122.75, 122.07, 120.03, 110.82. HRMS (FAB, m/z): [M$^+$] calcd. for C$_{52}$H$_{34}$N$_6$Si, 770.2614. found 770.2615. Anal. calcd for C$_{52}$H$_{34}$N$_6$Si: C, 81.01; H, 4.45; N, 10.90. found: C, 80.95; H, 4.75; N, 10.59.

EXAMPLE 9

6,6'-(4,4'-(9H-fluorene-9,9-diyl)bis(4,1-phenylene)) bis(6H-indolo[2,3-b]quinoxaline) (hereinafter abbreviated as FINQ, yield rate: 81%)

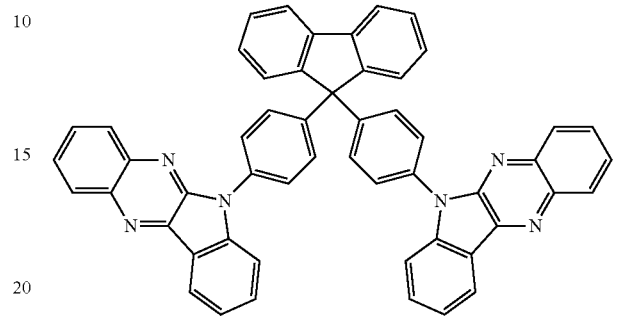

$^1$H NMR (400 MHz, CDCl$_3$, δ[ppm]): 8.52 (d, J=7.6 Hz, 2H), 8.30 (m, 2H), 8.08 (m, 2H), 7.87 (d, J=7.2 Hz, 2H), 7.74-7.66 (m, 8H), 7.64-7.55 (m, 10H), 7.48-7.39 (m, 6H). $^{13}$C NMR (100 MHz, CDCl$_3$, δ[ppm]): 150.61, 145.75, 145.22, 144.61, 140.52, 140.33, 140.20, 139.77, 134.15, 131.04, 129.58, 129.25, 128.90, 128.17, 128.10, 128.01, 126.74, 126.58, 126.48, 122.71, 121.95, 120.51, 119.88, 110.79. HRMS (FAB, m/z): [M$^+$] calcd. for C$_{53}$H$_{32}$N$_6$, 752.2688. found 752.2687. Anal. calcd for C$_{53}$H$_{32}$N$_6$: C, 84.55; H, 4.28; N, 11.16. found: C, 84.55; H, 4.39; N, 10.89.

EXAMPLE 10

6-(3-(diphenylphosphoryl)phenyl)-6H-indolo[2,3-b] quinoxaline (hereinafter abbreviated as m-INQPO, yield rate: 78%)

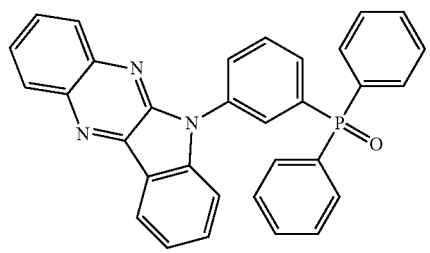 [SMILES: O=P(c1ccccc1)(c1ccccc1)c1cccc(-n2c3ccccc3c3nc4ccccc4nc32)c1]

$^1$H NMR (400 MHz, CDCl$_3$, δ[ppm]): 8.53 (d, J=7.6 Hz, 1H), 8.31 (d, J=8.0 Hz, 1H), 8.01 (m, 3H), 7.89 (m, 1H), 7.77 (m, 7H), 7.49 (m, 9H). $^{31}$P NMR (162 MHz, CDCl$_3$, δ[ppm]): 28.83.

EXAMPLE 11

6-(4-(diphenylphosphoryl)phenyl)-6H-indolo[2,3-b]quinoxaline (hereinafter abbreviated as p-INQPO, yield rate: 83%)

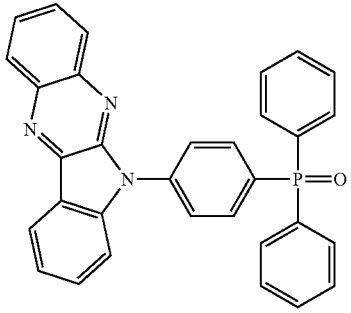 [SMILES: O=P(c1ccccc1)(c1ccccc1)c1ccc(-n2c3ccccc3c3nc4ccccc4nc32)cc1]

$^1$H NMR (400 MHz, CDCl$_3$, δ[ppm]): 8.57 (d, J=7.6 Hz, 1H), 8.34 (m, 1H), 8.07 (m, 1H), 7.95 (m, 4H), 7.77 (m, 6H), 7.61 (m, 4H), 7.53 (m, 4H), 7.46 (m, 1H). $^{31}$P NMR (162 MHz, CDCl$_3$, δ[ppm]): 29.01.

TABLE 1

The measured physical properties of examples 1 to 11 containing 6H-indolo[2,3-b]quinoxaline derivatives

| | $\lambda^a_{abs}$ [nm] | $\lambda^b_{em}$ [nm] | $\lambda^c_{em}$ [nm] | LUMO; HOMO$^d$ [eV] | $E_g$ [eV] | $E_T^e$ [eV] | $T_g^f$ |
|---|---|---|---|---|---|---|---|
| m-INQBz | 337, 353, 395 | 465 | 470 | 3.1; 6.0 | 2.9 | 2.3 | 113.73 |
| m-INQCz | 338, 353, 397 | 463 | 471 | 2.8; 5.7 | 2.9 | 2.3 | 105.85 |
| mDINQ | — | — | — | 2.8; 5.9 | 2.9 | — | — |
| m-INQDA | 337, 354, 395 | 554 | 499 | 2.5; 5.4 | 2.9 | 2.3 | — |
| p-INQSi | 338, 354, 397 | 472 | 468 | 3.0; 5.9 | 2.9 | 2.3 | 104.63 |
| p-INQCz | 339, 354, 395 | 509 | 475 | 2.4; 5.3 | 2.9 | 2.3 | 120.33 |
| p-INQDA | 355, 403 | — | 522 | 2.6; 5.3 | 2.7 | 2.3 | 96.15 |
| 2INQ | 338, 354, 398 | 468 | 484 | 2.8; 5.9 | 3.1 | 2.3 | 171.12 |
| FINQ | 338, 354, 398 | 477 | 471 | 2.7; 5.9 | 3.2 | 2.3 | 206.63 |
| m-INQPO | 338, 354, 396 | 462 | 472 | 3.2; 6.1 | 2.9 | 2.3 | — |
| p-INQPO | 338, 354, 394 | 462 | 471 | 3.2; 6.1 | 2.9 | 2.3 | — |

$^a$UV-vis absorption is measured by using CH$_2$Cl$_2$ as the solvent and the solution concentration is about 1 × 10$^{-5}$ M;
$^b$Photoluminescence is measured by using CH$_2$Cl$_2$ as the solvent and the solution concentration is about 1 × 10$^{-5}$ M;
$^c$Photoluminescence of powder;
$^d$Redox measurement is carried out in CH$_2$Cl$_2$ with solution concentration of about 1 × 10$^{-3}$ M with cyclic voltammetry (CV) for HOMO and LUMO estimation and the reported value is the value corresponding to Cp$_2$Fe/Cp$_2$Fe$^+$ under 4.8 eV of vacuum level;
$^e$2-Methyltetrahydrofuran is used as the solvent and the measurement is carried out at 77 K;
$^f$T$_g$: Glass transition temperature Referring to Table 1, the compounds of present invention have wavelengths of about 460~550 nm and may be used for preparing red OLED, green OLED, red phosphorescent OLED or green phosphorescent OLED.

Refer to FIG. 1, which is a schematic diagram illustrating an organic light emitting device containing 6H-indolo[2,3-b]quinoxaline derivatives according to one embodiment of the present invention. The light emitting device includes an emitting layer 3 configured between the anode 1 and cathode 2. The emitting layer 3 is made of host emitting material doped with light emitting material. The light emitting device may also include a hole transport layer 4, an electron blocking layer 9, an emitting layer 3, an hole blocking layer 6, an electron transport layer 5 and an electron injecting layer 8 sequentially configured on top of the anode 1. The real thickness of each layer doesn't correspond to the schematic size, and electron blocking layer 9, hole blocking layer 6 and electron injecting layer 8 may be optional. It is noted that the 6H-indolo[2,3-b]quinoxaline derivatives may be a host emitting material or a dopant in the emitting layer; the 6H-indolo[2,3-b]quinoxaline derivatives may be a hole transport material in the hole transport layer; the 6H-indolo[2,3-b]quinoxaline derivatives may be an electron transport material in the electron transport material; the 6H-indolo[2,3-b]quinoxaline derivatives may be an hole blocking material in the hole blocking layer; the 6H-indolo[2,3-b]quinoxaline derivatives may be an electron blocking material in the electron blocking layer; the 6H-indolo[2,3-b]quinoxaline derivatives may be a hole injecting material in the hole injecting layer; or the 6H-indolo[2,3-b]quinoxaline derivatives may be an electron injecting material in the electron injecting layer.

Example of Electroluminescent Devices

In the tested electroluminescent devices, the substrate is made of ITO; tested electrode materials include LiF/Al; tested emitting materials include (piq)$_2$Ir(acac) (iridium(III) bis (1-(phenyl)isoquinolinato-C$^2$,N)-acetylanetonate), Ir(piq)$_3$ (iridium(III)tri(1-(phenyl)isoquinolinato-C$^2$,N)), Ir15 (iridium(III) bis(4-methyl-2-(thiophen-2-yl)quinolinato-C$^3$,N)-acetylacetonate), (btp)$_2$Ir(acac) (iridium(III) bis (2-2'-benzo[4,5-α]thienyl)pyridinato-C$^3$,N)-acetylacetonate) and Ir6 (iridium(III) bis(4-methyl-2-(naphthalen-1-yl) quinolinato-C$^2$,N)-acetylacetonate); BCP (2,9-dimethyl-4,7-diphenyl-[1,10]phenanthroline) and Alq$_3$ (tris(8-hydroxyquinoline)aluminum(III) which can be used for the hole blocking layer or simultaneously hole blocking layer and electron transport layer. The tested hole transporting materials include NPB (4,4'-bis[N-(1-naphthyl)-N-phenyl-amino] biphenyl), and TCTA (4,4',4''-tri(N-carbazolyl)triphenylamine), which can be used for the hole blocking layer or simultaneously electron blocking layer and hole transport layer. The detailed structures of the tested devices are as follows:

Device A: NPB(20 nm)/TCTA(10 nm)/m-INQBz: 7% (piq)$_2$Ir(acac)(30 nm)/BCP(15 nm)/Alq(50 nm)/LiF(1 nm)/Al(100 nm)

Device B: NPB(20 nm)/TCTA(10 nm)/m-INQCz: 7% (piq)$_2$Ir(acac)(30 nm)/BCP(15 nm)/Alq(50 nm)/LiF(1 nm)/Al(100 nm)

Device C: NPB(20 nm)/TCTA(10 nm)/mDINQ: 7% (piq)$_2$Ir (acac)(30 nm)/BCP(15 nm)/Alq(50 nm)/LiF(1 nm)/Al (100 nm)

Device D: NPB(20 nm)/TCTA(10 nm)/m-INQDA: 7% (piq)$_2$Ir(acac)(30 nm)/BCP(15 nm)/Alq(50 nm)/LiF(1 nm)/Al(100 nm)

Device E: NPB(20 nm)/TCTA(10 nm)/p-INQSi: 7% (piq)$_2$Ir (acac)(30 nm)/BCP(15 nm)/Alq(40 nm)/LiF(1 nm)/Al (100 nm)

Device F: NPB(20 nm)/TCTA(10 nm)/p-INQSi: 7% (piq)$_2$Ir(acac)(30 nm)/BCP(15 nm)/Alq(50 nm)/LiF(1 nm)/Al(100 nm)

Device G: NPB(20 nm)/TCTA(10 nm)/p-INQCz: 7% (piq)$_2$Ir(acac)(30 nm)/BCP(15 nm)/Alq(50 nm)/LiF(1 nm)/Al(100 nm)

Device H: NPB(20 nm)/TCTA(10 nm)/p-INQDA: 7% (piq)$_2$Ir(acac)(30 nm)/BCP(15 nm)/Alq(50 nm)/LiF(1 nm)/Al(100 nm)

Device I: NPB(20 nm)/TCTA(10 nm)/2INQ: 1% (piq)$_2$Ir(acac)(30 nm)/BCP(15 nm)/Alq(50 nm)/LiF(1 nm)/Al(100 nm)

Device J: NPB(20 nm)/TCTA(10 nm)/2INQ: 4% (piq)$_2$Ir(acac)(30 nm)/BCP(15 nm)/Alq(50 nm)/LiF(1 nm)/Al(100 nm)

Device K: NPB(20 nm)/TCTA(10 nm)/2INQ: 7% (piq)$_2$Ir(acac)(30 nm)/BCP(15 nm)/Alq(50 nm)/LiF(1 nm)/Al(100 nm)

Device L: NPB(20 nm)/TCTA(10 nm)/2INQ: 7% (piq)$_2$Ir(acac)(30 nm)/BCP(15 nm)/Alq(40 nm)/LiF(1 nm)/Al(100 nm)

Device M: NPB(20 nm)/TCTA(10 nm)/2INQ: 7% (piq)$_2$Ir(acac)(30 nm)/BCP(15 nm)/Alq(60 nm)/LiF(1 nm)/Al(100 nm)

Device N: NPB(20 nm)/TCTA(10 nm)/2INQ: 7% Ir15(30 nm)/BCP(15 nm)/Alq(70 nm)/LiF(1 nm)/Al(100 nm)

Device O: NPB(20 nm)/TCTA(10 nm)/2INQ: 1% Ir15(30 nm)/BCP(15 nm)/Alq(50 nm)/LiF(1 nm)/Al(100 nm)

Device P: NPB(20 nm)/TCTA(10 nm)/2INQ: 4% Ir15(30 nm)/BCP(15 nm)/Alq(50 nm)/LiF(1 nm)/Al(100 nm)

Device Q NPB(20 nm)/TCTA(10 nm)/2INQ: 7% Ir15(30 nm)/BCP(15 nm)/Alq(50 nm)/LiF(1 nm)/Al(100 nm)

Device R NPB(20 nm)/TCTA(10 nm)/2INQ: 7% Ir(piq)$_3$(30 nm)/BCP(15 nm)/Alq(50 nm)/LiF(1 nm)/Al(100 nm)

Device S NPB(20 nm)/TCTA(10 nm)/2INQ: 7% (btp)$_2$Ir(acac) (30 nm)/BCP(15 nm)/Alq(50 nm)/LiF(1 nm)/Al(100 nm)

Device T: NPB(20 nm)/TCTA(10 nm)/FINQ: 1% (piq)$_2$Ir(acac)(30 nm)/BCP(15 nm)/Alq(50 nm)/LiF(1 nm)/Al(100 nm)

Device U: NPB(20 nm)/TCTA(10 nm)/FINQ: 4% (piq)$_2$Ir(acac)(30 nm)/BCP(15 nm)/Alq(50 nm)/LiF(1 nm)/Al(100 nm)

Device V: NPB(20 nm)/TCTA(10 nm)/FINQ: 7% (piq)$_2$Ir(acac)(30 nm)/BCP(15 nm)/Alq(50 nm)/LiF(1 nm)/Al(100 nm)

Device W NPB(20 nm)/TCTA(10 nm)/FINQ: 7% Ir(piq)$_3$(30 nm)/BCP(15 nm)/Alq(50 nm)/LiF(1 nm)/Al(100 nm)

Device X NPB(20 nm)/TCTA(10 nm)/FINQ: 7% (btp)$_2$Ir(acac) (30 nm)/BCP(15 nm)/Alq(50 nm)/LiF(1 nm)/Al(100 nm)

Device Y NPB(20 nm)/TCTA(10 nm)/2INQ: 7% Ir6 (30 nm)/BCP(15 nm)/Alq(50 nm)/LiF(1 nm)/Al(100 nm)

Device Z NPB(20 nm)/TCTA(10 nm)/DPINQ: 7% (piq)$_2$Ir(acac) (30 nm)/BCP(15 nm)/Alq(50 nm)/LiF(1 nm)/Al(100 nm)

Device Z' NPB(20 nm)/TCTA(10 nm)/TPINQ: 7% (piq)$_2$Ir(acac) (30 nm)/BCP(15 nm)/Alq(50 nm)/LiF(1 nm)/Al(100 nm)

Device Z" NPB(20 nm)/TCTA(10 nm)/p-INQPO: 7% (piq)$_2$Ir(acac) (30 nm)/BCP(15 nm)/Alq(50 nm)/LiF(1 nm)/Al(100 nm)

Comparison of the Device Performance

TABLE 2

Comparison of the performance of the electroluminescent devices

| | $V_d^a$ | $L_{max}^b$ (Cd/m$^2$) | $\eta_{ext}^c$(%) | $\eta_c^d$(Cd/A) | $\eta_p^e$ (lm/W) | $\lambda_{max}^f$ | CIE@8 V |
|---|---|---|---|---|---|---|---|
| A | 3.0 V | 47095 @14 V | 17.3@ 5 V | 19.5 @5 V | 16.5 @3 V | 626 nm | (0.68, 0.32) |
| B | 3.6 V | 59150 @13 V | 19.2@4.5 V | 22.2 @4.5 V | 17.2 @4 V | 624 nm | (0.67, 0.33) |
| C | 3.4 V | 63165 @13 V | 20.2@4.5 V | 24 @5 V | 20.3@3.5 V | 623 nm | (0.67, 0.33) |
| D | 2.9 | 65916 @13.5 V | 20.2@4.0 V | 23.3 @4.5 V | 21.2 @3 V | 624 nm | (0.68, 0.32) |
| E | 2.8 V | 52880 @14 V | 22.8@ 4 V | 28.6 @4 V | 25 @3.5 V | 619 nm | (0.67, 0.33) |
| F | 2.7 V | 64335 @12.5 V | 19.7@4.5 V | 24.8 @5 V | 23.1 @3 V | 622 nm | (0.67, 0.33) |
| G | 3.1 V | 70126 @ 12.5 V | 20.4 @ 5.5 V | 27.3 @ 6.0 V | 21.5 @ 3.5 V | 622 nm | (0.67, 0.33) |
| H | 2.6 V | 63617 @13.5 V | 22.7 @ 4.5 V | 25.8 @ 4.5 V | 22.7 @ 3.0 V | 623 nm | (0.68, 0.32) |
| I | 3.6 V | 59745 @14 V | 24.2@ 5 V | 32.5@5 V | 20.4 @ 5 V | 618 nm | (0.67, 0.33) |
| J | 3.1 V | 62777 @15 V | 26.7 @4 V | 32.5@4 V | 29.0 @ 3.5 V | 620 nm | (0.67, 0.33) |
| K | 2.7 V | 64478 @12 V | 23.2 @3 V | 26.2 @3 V | 27.6 @ 3 V | 623 nm | (0.68, 0.32) |
| L | 2.9 V | 62563 @14 V | 22.2@ 5 V | 25.3 @5 V | 22.5 @ 3 V | 624 nm | (0.68, 0.32) |
| M | 2.7 V | 62210 @ 14.5 V | 23.4 @3 V | 25.8 @3 V | 27.0 @ 3 V | 626 nm | (0.68. 0.32) |
| N | 2.7 V | 60953 @ 13.5 V | 22.0 @4.5 V | 25.5 @5 V | 24.8 @ 3 V | 624 nm | (0.68. 0.32) |
| O | 3.8 V | 51028 @13.5 V | 30.9@ 4 V | 47.0@4 V | 37.0 @ 4 V | 614 nm | (0.66, 0.34) |
| P | 3.1 V | 54471 @14.0 V | 28.6 @4 V | 40.5@4 V | 31.9 @ 4 V | 616 nm | (0.67, 0.33) |
| Q | 3.1 V | 59929 @13.5 V | 24.8 @4 V | 35.3@4 V | 30.5 @ 3.5 V | 616 nm | (0.67, 0.33) |

TABLE 2-continued

Comparison of the performance of the electroluminescent devices

| | $V_d{}^a$ | $L_{max}{}^b$ (Cd/m²) | $\eta_{ext}{}^c$(%) | $\eta_c{}^d$(Cd/A) | $\eta_p{}^e$ (lm/W) | $\lambda_{max}{}^f$ | CIE@8 V |
|---|---|---|---|---|---|---|---|
| R | 3.4 V | 60376 @14.5 V | 17.8@ 5.0 V | 21.5 @5.0 V | 17.2 @ 3.5 V | 621 nm | (0.67, 0.33) |
| S | 3.2 V | 25636 @14 V | 15.0@ 4.5 V | 19.0 @4.5 V | 16.6 @ 3.5 V | 617 nm | (0.68, 0.32) |
| T | 3.1 V | 63298 @13 V | 21.1@ 4.5 V | 23.6 @4.5 V | 19.5 @ 3.5 V | 626 nm | (0.68, 0.32) |
| U | 3.1 V | 64417 @13.5 V | 22.4 @5 V | 25.3 @5 V | 18.8 @ 4 V | 626 nm | (0.68, 0.32) |
| V | 3.1 V | 61056 @ 12.5 V | 22.3 @4.5 V | 24.2@4.5 V | 19.9@ 3.5 V | 625 nm | (0.68. 0.32) |
| W | 3.3 V | 24106 @ 14.5 V | 22.3 @4.5 V | 24.2@4.5 V | 19.9@ 3.5 V | 625 nm | (0.68. 0.32) |
| X | 3.6 V | 57248 @15.0 V | 13.9 @5 V | 17.3 @5 V | 12.6 @ 4 V | 618 nm | (0.68, 0.32) |
| Y | 2.8 V | 42550 @ 13.5 V | 14.8 @ 5 V | 14.3 @5 V | 13.6 @ 3 V | 629 nm | (0.69, 0.31) |
| Z | 3.1 V | 64429 @ 12.5 V | 19.6 @ 5 V | 22.1 @ 5.5 V | 18.7 @ 3.5 V | 625 nm | (0.68, 0.32) |
| Z' | 3.6 V | 62353 @ 14.5 V | 25.5 @ 6.5 V | 27.7 @ 6.5 V | 18.9 @ 4.5 V | 625 nm | (0.68, 0.32) |
| Z" | 2.4 V | 45369 @ 13.5 V | 19.9 @ 2.5 V | 22.3 @ 2.5 V | 28.1 @ 2.5 V | 624 nm | (0.68, 0.32) |

$^a V_d$: Drive voltage;
$^b L_{max}$: maximum luminescence;
$^c \eta_{ext}$: maximum external quantum efficiency;
$^d \eta_c$: maximum current efficiency;
$^e \eta_p$: maximum power efficiency; and
$^f \lambda_{max}$: maximum emission wavelength To sum up, the 6H-indolo[2,3-b]quinoxaline derivatives of the present invention incorporate an indole and a quinoxaline group therefore inherit high thermal stability and good energy transfer ability from indole and good electron-injection ability from quinoxaline and may be used for the host emitting material, guest emitting material, electron transfer material or hole transfer material.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A 6H-indolo[2,3-b]quinoxaline derivative comprising a chemical formula represented by Formula (II), DPINQ, TPINQ or FINQ:

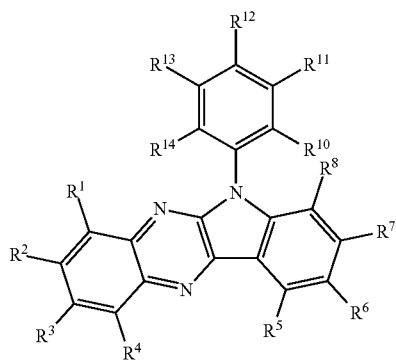

(II)

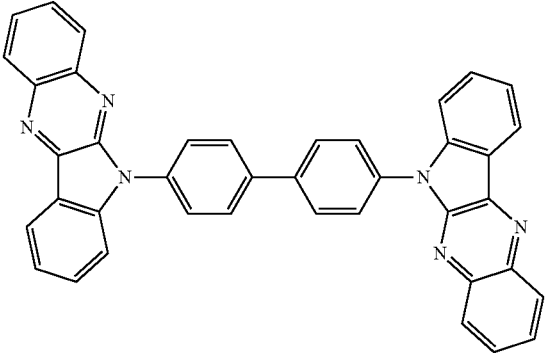

DPINQ

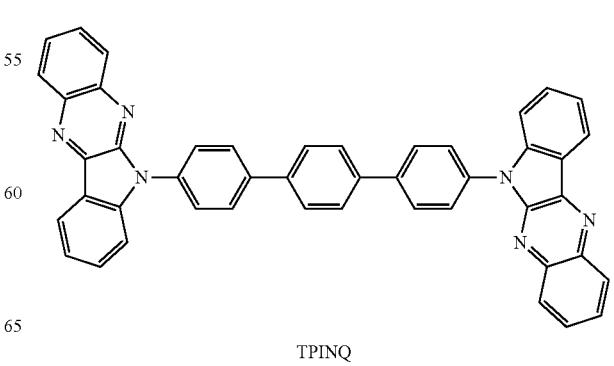

TPINQ

-continued

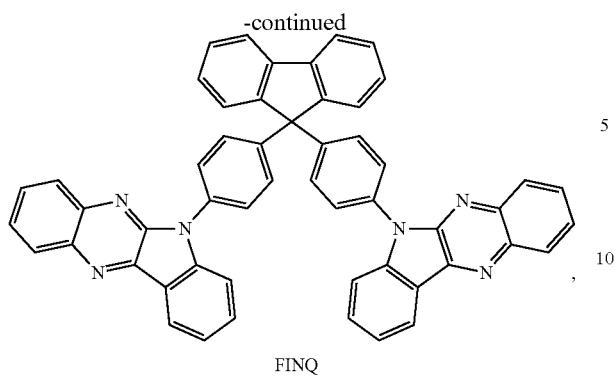

FINQ wherein each of $R^1$ to $R^8$, $R^{10}$ to $R^{14}$ is independently selected from the group consisting of hydrogen, halogen, aryl group, alkenyl group, C1-C20 alkyl group, alkynyl group, cyano, trifluoromethyl, alkylamino, amino, alkoxy group, heteroaryl group, halogen substituted aryl group, halogen substituted aralkyl group, haloalkyl substituted aryl group, haloalkyl substituted aralkyl group, aryl substituted C1-C20 alkyl group, cycloalkyl group, C1-C20 alkoxy group, C1-C20 alkyl substituted amino group, haloalkyl substituted amino group, aryl substituted amino group, heteroaryl substituted amino group, aryl substituted phosphine oxide, C1-C20 alkyl substituted phosphine oxide, haloalkyl substituted phosphine oxide, halogen substituted phosphine oxide, heteroaryl substituted phosphine oxide, nitro group, carbonyl group, aryl substituted carbonyl group, heteroaryl substituted carbonyl group, and halogen substituted C1-C20 alkyl group, and at least one of $R^{11}$ to $R^{13}$ is selected from the group consisting of substituted or unsubstituted heteroaryl group, aryl or heteroaryl substituted boronic group, aryl or heteroaryl substituted silyl group and aryl or heteroaryl substituted phosphine oxide.

2. The 6H-indolo[2,3-b]quinoxaline derivative as claimed in claim 1, wherein at least one of $R^{11}$ to $R^{13}$ is independently selected from the group consisting of aryl or heteroaryl substituted boronic group, aryl or heteroaryl substituted silyl group and aryl or heteroaryl substituted phosphine oxide.

3. The 6H-indolo[2,3-b]quinoxaline derivative as claimed in claim 1, wherein at least one of $R^{11}$ to $R^{13}$ is selected from the group consisting of triphenylsilane and diphenylphosphine oxide

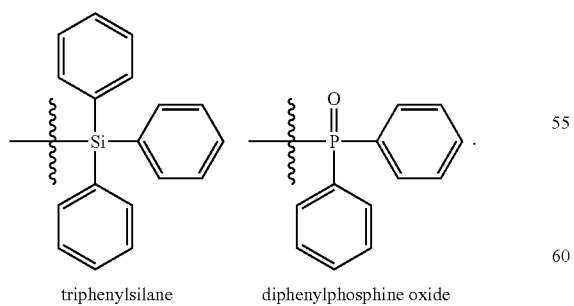

triphenylsilane    diphenylphosphine oxide

4. The 6H-indolo[2,3-b]quinoxaline derivative as claimed in claim 1, wherein at least one of $R^{11}$ to $R^{13}$ is selected from the group consisting of 6H-indolo[2,3-b]quinoxaline, 1-phenyl-1H-benzol[d]imidazole and 9H-carbazole

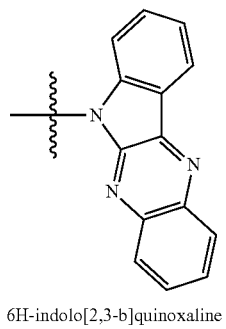

6H-indolo[2,3-b]quinoxaline

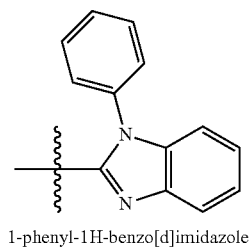

1-phenyl-1H-benzo[d]imidazole

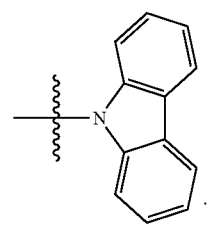

9H-carbazole

5. The 6H-indolo[2,3-b]quinoxaline derivative as claimed in claim 1, having a chemical formula represented as listed below

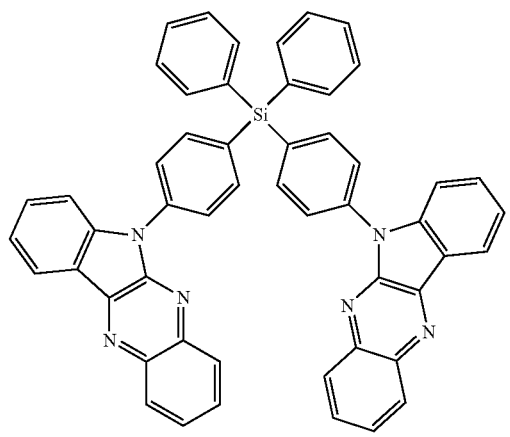

6. An organic light emitting diode, comprising:
a cathode;
an anode; and
an organic layer configured between the cathode and the anode and comprising a 6H-indolo [2,3-b]quinoxaline derivative comprising a chemical formula represented by Formula (II), DPINQ, TPINQ or FINQ:

(II)

DPINQ

TPINQ

FINQ wherein each of $R^1$ to $R^8$, $R^{10}$ to $R^{14}$ is independently selected from the group consisting of hydrogen, halogen, aryl group, alkenyl group, C1-C20 alkyl group, alkynyl group, cyano, trifluoromethyl, alkylamino, amino, alkoxy group, heteroaryl group, halogen substituted aryl group, halogen substituted aralkyl group, haloalkyl substituted aryl group, haloalkyl substituted aralkyl group, aryl substituted C1-C20 alkyl group, cycloalkyl group, C1-C20 alkoxy group, C1-C20 alkyl substituted amino group, haloalkyl substituted amino group, aryl substituted amino group, heteroaryl substituted amino group, aryl substituted phosphine oxide, C1-C20 alkyl substituted phosphine oxide, haloalkyl substituted phosphine oxide, halogen substituted phosphine oxide, heteroaryl substituted phosphine oxide, nitro group, carbonyl group, aryl substituted carbonyl group, heteroaryl substituted carbonyl group, and halogen substituted C1-C20 alkyl group, and at least one of $R^{11}$ to $R^{13}$ is selected from the group consisting of substituted or unsubstituted heteroaryl group, aryl or heteroaryl substituted boronic group, aryl or heteroaryl substituted silyl group and aryl or heteroaryl substituted phosphine oxide.

7. The organic light emitting diode as claimed in claim 6, wherein at least one of $R^{11}$ to $R^{13}$ is independently selected from the group consisting of aryl or heteroaryl substituted boronic group, aryl or heteroaryl substituted silyl group and aryl or heteroaryl substituted phosphine oxide.

8. The organic light emitting diode as claimed in claim 6, wherein at least one of $R^{11}$ to $R^{13}$ is selected from the group consisting of triphenylsilane and diphenylphosphine oxide

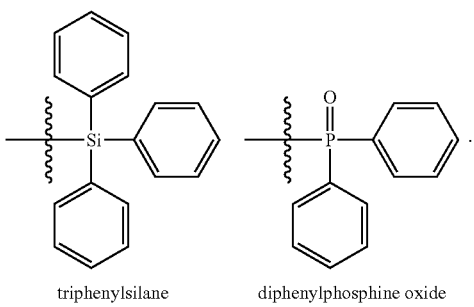 [SMILES: *[Si](c1ccccc1)(c1ccccc1)c1ccccc1 ; *P(=O)(c1ccccc1)c1ccccc1]

triphenylsilane    diphenylphosphine oxide

9. The organic light emitting diode as claimed in claim 6, wherein at least one of $R^{11}$ to $R^{13}$ is selected from the group consisting of 6H-indolo[2,3-b]quinoxaline,-1-phenyl-1H-benzol[d]imidazole and 9H-carbazole

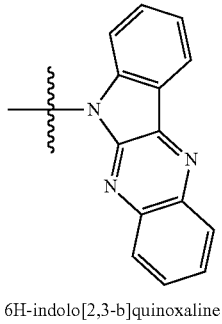

6H-indolo[2,3-b]quinoxaline

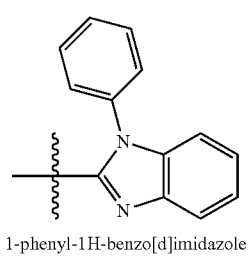

1-phenyl-1H-benzo[d]imidazole

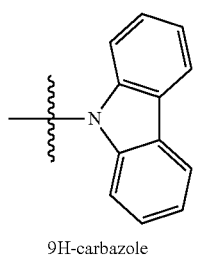

9H-carbazole

10. The organic light emitting diode as claimed in claim 6, wherein the 6H-indolo[2,3-b]quinoxaline derivative has a chemical formula represented as listed below

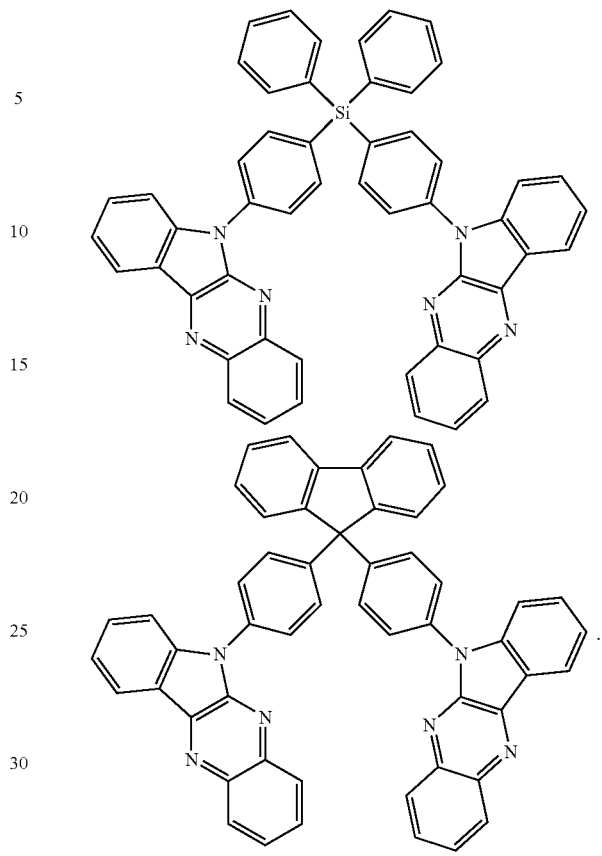

11. The organic light emitting diode as claimed in claim 6, wherein the organic layer comprises an emitting layer, and the 6H-indolo[2,3-b]quinoxaline derivative is a host emitting material.

12. The organic light emitting diode as claimed in claim 6, wherein the organic layer comprises an emitting layer, and the 6H-indolo[2,3-b]quinoxaline derivative is a dopant.

13. The organic light emitting diode as claimed in claim 6, wherein the organic light emitting diode comprises a red OLED, a green OLED, a red phosphorescent OLED or a green phosphorescent OLED.

14. The organic light emitting diode as claimed in claim 6, further comprising an emitting layer configured between the cathode and the anode.

15. The organic light emitting diode as claimed in claim 14, wherein the organic layer comprises a hole transport layer configured between the emitting layer and the anode, and the 6H-indolo[2,3-b]quinoxaline derivative is a hole transport material.

16. The organic light emitting diode as claimed in claim 14, wherein the organic layer comprises an electron transport layer configured between the emitting layer and the cathode, and the 6H-indolo[2,3-b]quinoxaline derivative is an electron transport material.

17. The organic light emitting diode as claimed in claim 14, wherein the organic layer comprises a hole transport layer configured between the emitting layer and the cathode, and the 6H-indolo[2,3-b]quinoxaline derivative is a hole blocking material.

18. The organic light emitting diode as claimed in claim 14, wherein the organic layer comprises an electron blocking layer configured between the emitting layer and the anode, and the 6H-indolo[2,3-b]quinoxaline derivative is an electron blocking material.

19. The organic light emitting diode as claimed in claim 14, wherein the organic layer comprises a hole injecting layer configured between the emitting layer and the anode, and the 6H-indolo[2,3-b]quinoxaline derivative is a hole injecting material.

20. The organic light emitting diode as claimed in claim 14, wherein the organic layer comprises an electron injecting layer configured between the emitting layer and the cathode, and the 6H-indolo[2,3-b]quinoxaline derivative is an electron injecting material.

* * * * *